United States Patent [19]

Nagy et al.

[11] Patent Number: 5,571,477
[45] Date of Patent: Nov. 5, 1996

[54] EQUIPMENT FOR SAMPLING AND WORK-UP FOR ANALYSIS OF PAH AND OTHER ORGANIC COMPOUNDS, AND HYDROGEN FLUORIDE AND SULPHUR OXIDES

[75] Inventors: Kalman Nagy, Trondheim; Trygve Foonæs, Årdalstangen; Herman Kolderup, Trondheim; Knut Bergli, Bødalen, all of Norway

[73] Assignee: Norsk Hydro A.S., Oslo, Norway

[21] Appl. No.: 114,310

[22] Filed: Sep. 2, 1993

[30]   Foreign Application Priority Data

Sep. 2, 1992 [NO] Norway ................................ 923420

[51] Int. Cl.$^6$ ........................... B01D 24/00; B01D 41/00
[52] U.S. Cl. ................. 422/88; 96/108; 96/109; 96/110; 96/112; 96/121; 96/135; 96/136
[58] Field of Search ................. 422/88; 436/140; 95/14, 23, 92, 93; 96/108, 109, 110, 112, 121, 135, 136

[56]   References Cited

U.S. PATENT DOCUMENTS

| H255 | 4/1987 | Genovese et al. | 424/9 |
|---|---|---|---|
| 3,735,562 | 5/1973 | Mousseau, Jr. et al. | 55/16 |
| 3,758,603 | 9/1973 | Steigelmann et al. | 260/677 |
| 4,133,309 | 1/1979 | Kohler et al. | 128/146.6 |
| 4,303,529 | 12/1981 | Huckins et al. | 210/635 |
| 4,666,856 | 5/1987 | Irgum et al. | 436/122 |
| 5,049,365 | 9/1991 | Okabayashi et al. | 423/245.1 |
| 5,053,142 | 10/1991 | Sorensen et al. | 210/742 |
| 5,087,360 | 2/1992 | Wright et al. | 210/198.2 |
| 5,135,548 | 8/1992 | Golden et al. | 55/25 |
| 5,147,538 | 9/1992 | Wright et al. | 210/198.2 |
| 5,205,154 | 4/1993 | Lee et al. | 73/23.35 |
| 5,271,903 | 12/1993 | Durst et al. | 422/101 |
| 5,300,138 | 4/1994 | Fischer et al. | 96/125 |

FOREIGN PATENT DOCUMENTS

| 0042683 | 12/1981 | European Pat. Off. . |
|---|---|---|
| 2448001 | 5/1975 | Germany . |
| 2083622 | 3/1983 | United Kingdom . |

*Primary Examiner*—Robert J. Warden
*Assistant Examiner*—N. Bhat
*Attorney, Agent, or Firm*—Wenderoth, Lind & Ponack

[57]   ABSTRACT

Equipment samples and processes for analysis PAH and other organic compounds, as well as hydrogen fluoride and sulphur oxides in air and in gas in production equipment.

The equipment comprises a layered adsorption device 1 in which the adsorbents are dry. During sampling, the adsorption device 1 is connected at its upper end to a probe 8, which is brought into contact with the object to be sampled, and connected at its lower end to a gel box 10, a pump 9 and a gas clock 12, in series. After sampling, the adsorption device 1 may be connected directly to an extraction apparatus 11 for the processing of the sample.

25 Claims, 4 Drawing Sheets

EQUIPMENT FOR SAMPLING AND WORK-UP FOR ANALYSIS OF PAH AND OTHER ORGANIC COMPOUNDS, AND HYDROGEN FLUORIDE AND SULPHUR OXIDES

BACKGROUND OF THE INVENTION

The present invention concerns equipment for sampling and processing for analysis PAH and other organic compounds, as well as hydrogen fluoride and oxides of sulphur.

PAH stands for polycyclic aromatic hydrocarbons. Many of these compounds are carcinogenic. Other compounds that are desirable to monitor because of their harmful effects include phenols, polychlorinated biphenyls (PCBs), and dioxins. All these compounds occur for example in tar and/or solvents.

It is known that hydrogen fluoride and sulphur oxides are environmental pollutants and health hazards.

The above-mentioned compounds occur, for example, to a greater or lesser extent, in and around anode factories, in raw gas from electrolytic furnaces, in electrolysis halls, in and around incineration plants, in solvents and in places of work where chemicals containing such compounds are used or formed.

Hitherto it has been difficult to monitor emissions of these compounds because the available measuring equipment has not been adequate. Present-day knowledge of the harmful environmental effects of such emissions, even in small quantities, has made it essential to conduct research on measuring equipment and analytical methods which can determine emissions of these compounds with sufficient accuracy.

Besides the desirability of measuring whether these compounds are emitted into the air, and if so in what quantities, it is also desirable in anode factories to be able to draw up material balance reports in the purification plants in order to survey the tar/PAH flow in the factories, and to measure the effect of the purification plants. The material which exists today to carry out such measurements in the anode factories does not provide reliable results, and there is a need for better solutions.

In 1986 Alcoa published its own method 4090A, among other things, measuring particles and hydrocarbon emission from anode factories, including gas to and from purification plants, in J. H. Walker, J. E. Gibb & J. N. Peace, "Sampling and analytical methods for measuring carbon plant emissions", *Light Metals,* pp. 955–972. This method is a modification of the EPA's reference method 5. The modification involves sampling through probe tubes and filters heated to approximately the temperature in the gas duct. The gas is then cooled and conducted through c. 20 g XAD adsorbent at 20° C. At this temperature the water vapour will condense. After adsorption, therefore, are a condensate trap (empty impinger) followed by two impingers with de-ionized water and one impinger with a drying agent (silica gel). All the impingers are in ice baths. After sampling, all the units are extracted, except the impinger with the drying agent, with methylene chloride. Alcoa's method is complicated because the sampling equipment consists of a relatively large number of collection units in series. This means that the processing and analysis of the samples becomes labour-intensive and has a high risk of error.

In a considerably simpler sampling method used by Hydro Aluminium, the gas sample is extracted through a pipe filled with glass wool (the "Lurgi method"). The gas is then conducted through two absorption flasks with toluene and one empty flask, and straight on into a pump with a gas clock. The flasks are not cooled, and the evaporation loss of the toluene is therefore high. After sampling, the glass wool is boiled out with toluene, filtered and evaporated. The absorption sample in the flasks is also filtered and evaporated. The particles in the solution are extracted with hot toluene, which is evaporated. The sum of the evaporation residues is specified as the total tar quantity. Tar contains a large number of components ranging from heavy to volatile compounds. The consumption of toluene with this method is 600–1000 ml per sampling. The boiling point of toluene is 110.6° C. This leads to great uncertainty in the method, inasmuch as the volatile compounds in tar will evaporate with the toluene. In addition, the evaporation of such quantities of toluene is undesirable, because the toluene vapour is toxic.

European patent application publ. no. 42683 describes an apparatus for capturing gas components in low concentrations. They are captured on various adsorbents which are packed between sinters in an outside pipe. The technique described in the above-mentioned European patent application would not, however, be suitable for determining the tar flow in an anode factory and for similar tasks where the present invention can be used. If one used the apparatus described in EP-42683 for such purposes, problems would arise because the gas volume through the apparatus is too small for isokinetic sampling, and aerosols would not be captured quantitatively. In addition, this technique would entail condensation of water vapour, and it would not be possible to change the adsorbent after sampling.

British patent application publ. no. 2083662 describes an apparatus where fluid is used as an absorption medium to capture gas components. This apparatus could not be used either to determine the tar flow in an anode factory, since the hydrophobic filter would quickly be clogged with tar and the fluid in the pipe would not absorb gaseous tar components quantitatively. Furthermore, the fluid would evaporate or water vapour would condense, depending on the temperature conditions, and this equipment cannot be extracted directly after the sampling.

The same disadvantages from which the technique according to GB-2083662 suffers as regards use in sampling to determine tar content also apply to the apparatus described in German patent document no. 2448001. This German patent application describes an apparatus with specially impregnated filters in series for selective separation of gas components ($Cl_2$, $H_2S$, $SO_2$) from air.

SUMMARY OF THE INVENTION

The object of the present invention is therefore to procure sampling and processing equipment for gas which can produce a product which can be analysed for content of PAH, other hydrocarbons, hydrogen fluoride and sulphur oxides in a simple, reliable manner, and which does not suffer from the above-mentioned disadvantages.

The sampling equipment in accordance with the invention is based on solid adsorbents designed in a sandwich structure. This unit, which for example could take the form of a cylinder or housing of metal, plastic, teflon or glass, can further be connected with a special extractor without any kind of dismantling, for direct extraction of the organic compounds which have been captured. The specially designed extraction apparatus works on the soxhlet principle, i.e. several rinses with stripped solvent. The extraction agents used are organic solvents, mainly dichloromethane. The organic compounds can then be analysed by means of analytical methods such as chromatography or spectrometry after a suitable processing procedure.

With this equipment one achieves a better method of sampling the above-mentioned organic compounds than the method described with the prior art. Furthermore, the equipment as specified in the invention involves a processing procedure which is less labour-intensive and more accurate than the known technique.

For sampling hydrogen fluoride and sulphur oxides, special adsorbents are used, such as activated aluminium oxide. For extraction of inorganic compounds, water-based solvents are used.

As regards the use of the equipment of the invention in anode factories in particular, it facilitates detailed studies of what happens during the purification process. The composition and quantity of PAH/Tar from the anode furnaces in incoming and outgoing gas from the various parts of the purification plants can be determined by using this equipment.

One of the advantages of the sampling equipment of the present invention compared with the known technique is that it is more compact. The reason why such a compact design is possible is that solid adsorbents are used. For industrial hygiene purposes it may also be appropriate to make the sampling equipment portable. This can be done by means of simple modifications, such as by miniaturizing the equipment and integrating it in a cycle such that it can be carried as one unit. The equipment can also be further automated by means of a microprocessor.

Another advantageous feature of using solid, dry adsorbents in the equipment is that there is thus no need to evaporate away quantities of organic solvents which are toxic, as is the case when absorption solutions are used. In addition, the adsorbents are regenerated during the extraction procedure, and can be used again.

The adsorption agents used depend on the samples one wishes to take. The adsorption device, which makes up an essential part of the sampler, is built up from the required number of elements. The elements are screwed together, and the adsorption agents which are placed in the various elements may be the same, or different. Suitable adsorbents are aluminium oxide, silica gel and hydrophobic polymers, for example Tenax, XAD 2 and XAD 4. For sampling in anode factories, the adsorbent XAD 2 is preferred. Tenax, which is also used as an adsorption material in chromatography columns, is a very good adsorption agent. However, it is much more expensive than, for example, XAD 2, but for special purposes it will be relevant to use this adsorption agent. For sampling with a view to analysis of hydrogen fluoride, aluminium oxide is preferred as the adsorption material.

Adsorption materials, which may contain organic compounds to begin with, must be cleaned to remove these compounds before use in the sampling equipment. Such cleaning must be done by using XAD 2, for example, as an adsorbent.

For sampling heated gases, as in anode factories, the temperature in the adsorption equipment is kept so high that the gas will not cool down to room temperature and cause condensation of water vapour on the adsorbents. By preventing water vapour condensation on the adsorbents, one ensures that the adsorption capacity is not destroyed and prevents the extraction and analysis procedure becoming more complicated. Instead, the water is captured in a silica gel adsorbent which is connected to the adsorption device.

Because the adsorption device can be placed directly in the extraction equipment after the sample has been taken, one avoids the several steps required for processing when using the previously-known techniques. This means that an analysis of the products procured by using the equipment as specified in the present invention involves less risk of error than does the use of equipment according to the prior art.

According to the known technique, toluene, among other things, which has a boiling point of 110.6° C., is used as an extraction agent during the processing. In the extraction process as specified in the present invention, the preferred extraction agent is dichloromethane, with a boiling point of 40° C. When the extraction agent is evaporated after extraction, one will have isolated the bulk of the organic compounds which have a higher boiling point than 40° C. Using toluene, one loses the organic compounds which have lower boiling points than 110.6° C., and light organic compounds are expelled uncontrollably during the evaporation. These light compounds thus cannot be subjected to analysis either.

If one wishes to analyse any organic compounds with lower boiling points than 40° C. which might be present, one can use an extraction agent which has a lower boiling point than 40° C.

BRIEF DESCRIPTION OF THE DRAWINGS

A more detailed description of the invention is given below with references to the accompanying drawings. Also given are test data showing the appropriateness and accuracy of the equipment compared with those of the prior art.

DETAILED DESCRIPTION OF THE PREFERRED EMBODIMENTS

Figure 1:
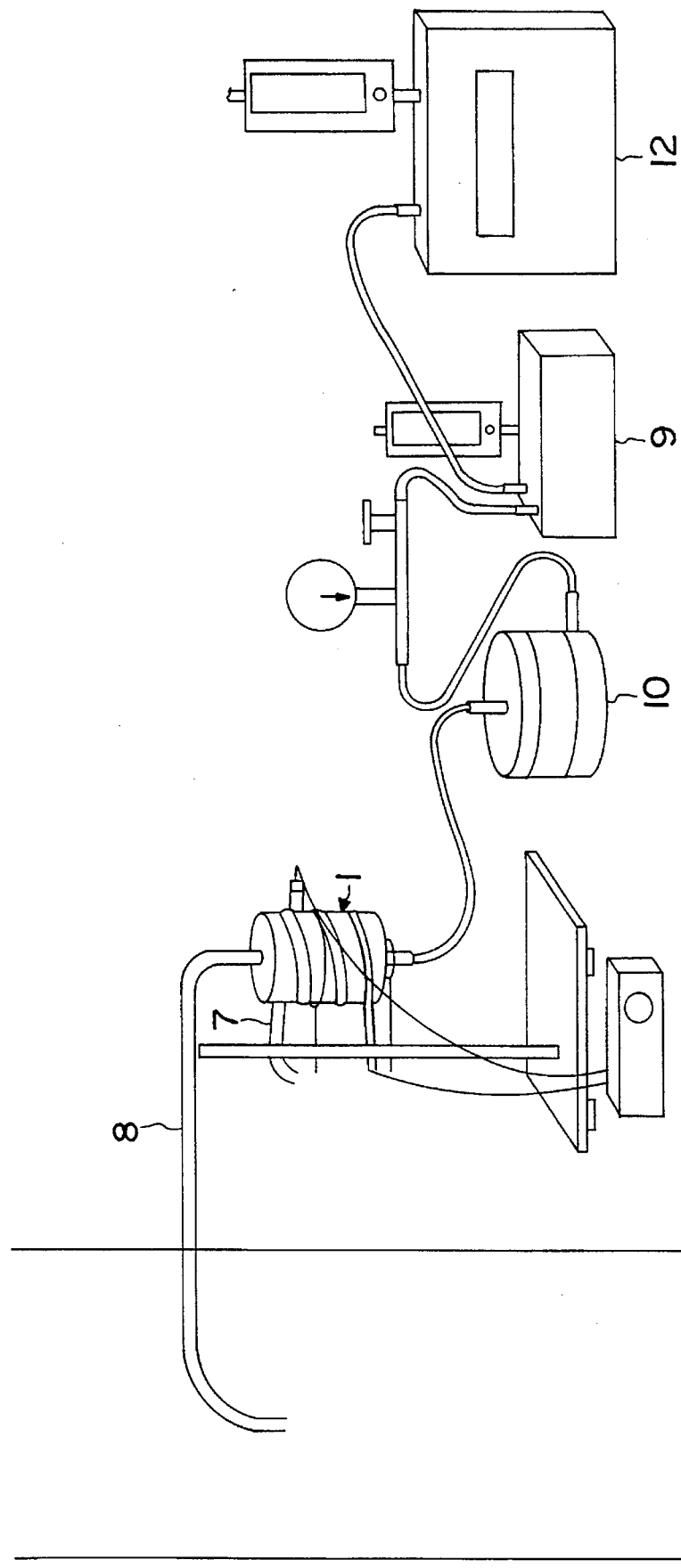
FIG. 1 is an overview of equipment according to the present invention during sampling.
Figure 2:
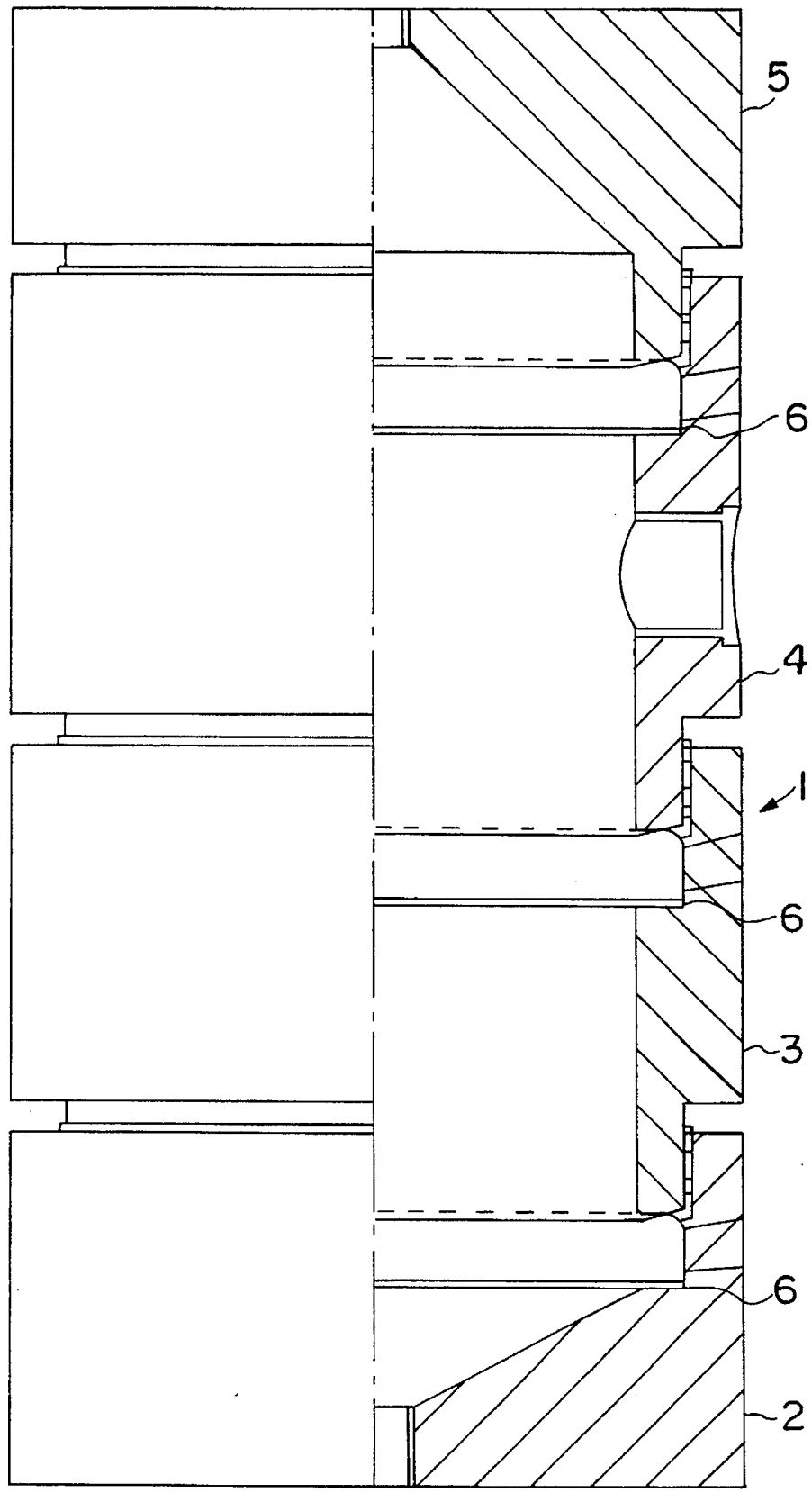
FIG. 2 is a schematic overview of an adsorption device in the equipment of FIG. 1.
Figure 3:
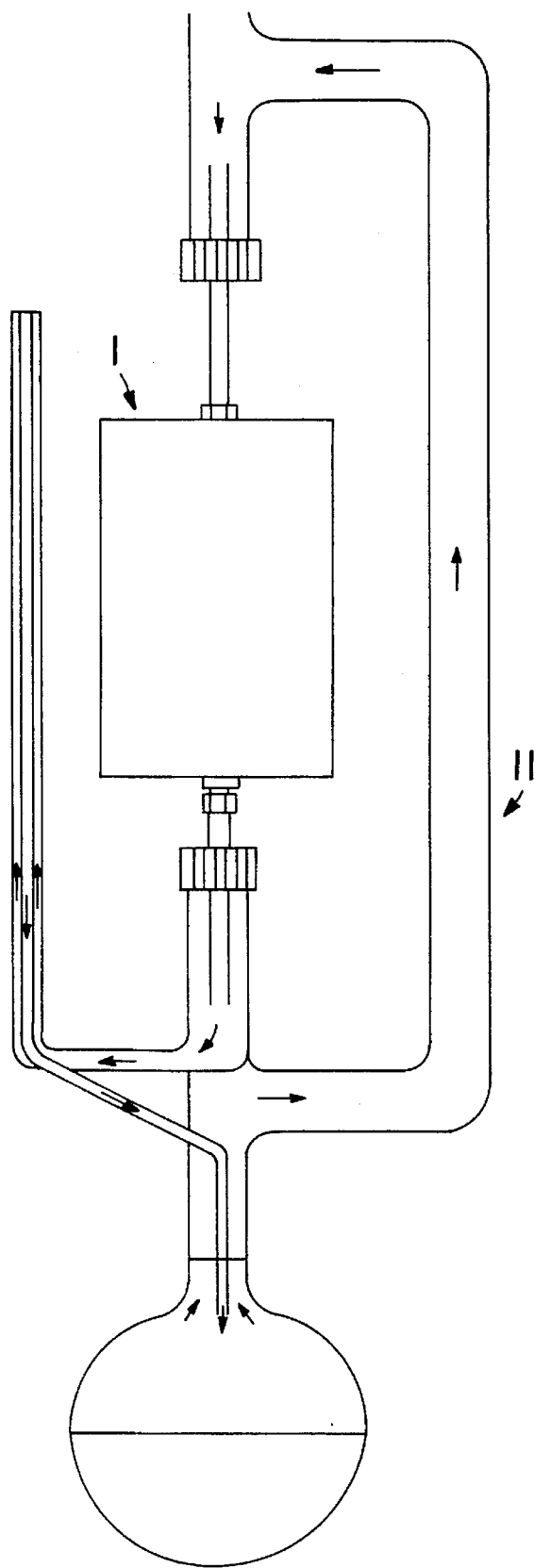
FIG. 3 is a sketch of the equipment of FIG. 1 during processing of a sample.

Elements 1–12 in FIGS. 1–3 stand for:

1: adsorption device
2: bottom
3: middle piece
4: middle piece with hole for thermoelement
5: top
6: netting or grille
7: heating element
8: probe
9: pump
10: gel box
11: extraction device
12: gas clock During the actual sampling, the equipment consists of an adsorption device 1 which has an opening at both ends. To the upper end of the adsorption device is connected a probe 8 and to the lower end is connected a gel box 10, a pump 9 and a gas clock 12 in series. This is shown in FIG. 1.

The adsorption device 1 is layered, and is built up of the following elements: a bottom 2, one or more middle pieces 3, one or more middle pieces 4 furnished with a hole in the side, and a top 5. All the elements are cylindrical, and threaded at both ends, where the threads in the upper part of the top 5 and the lower part of the bottom 2 are inside, and the device 1 is built up such that the bottom 2, a required number of middle pieces 3 and, 4 placed in the required order, and the top 5 are screwed together. It may be necessary to use sealing devices between the elements to prevent leakage from the device 1. The layers in the device 1 are separated by netting or a grille 6. Filter paper or glass wool can be laid on one or more of the grilles 6, if required, and collect particulate material. The middle pieces 3, 4 are filled with the required adsorption agents before the arrangement 1 is screwed together. The middle pieces 3, and 4 are filled with the same or different adsorbents. Normally, however, only one middle piece 4 will be necessary, with the main adsorbent, and below it a middle piece 3 with an adsorbent which constitutes a control layer. When one is sampling large quantities of tar, for example from uncleaned gas, it may be appropriate to place an extra middle piece 3, filled with filtering filler material for rough separation over the middle piece 4 before the top 5 is screwed on. The hole in the middle piece 4 may be sealed with a thermoelement or a screw stopper. When one is sampling, the temperature control in the adsorption device 1 will be important, and a thermoelement can then be placed in the hole. When one is processing the sample, the thermoelement can be replaced with a screw stopper, since the temperature is controlled by other means in this procedure, A sketch of the adsorption device is shown in FIG. 2.

The opposite end of the probe 8, which is screwed onto the upper end of the adsorption device 1, is conducted to the object to be sampled. The adsorption arrangement 1 is heated up by a heating element 7 such that water in the object to be sampled is not condensed out into the arrangement 1. The heating element 7 can, for example, consist of heating tape. The gel box 10, which for example can consist of a drying flask with silica gel, is connected to the adsorption device 1 at its lower end. The function of the gel box is to collect any water which may be present in the gas which is being sampled. The gel box 10 and the pump 9 are connected via an adjustment valve. The pump 9 can for example consist of a leak-proof membrane pump, which is further connected to a gas clock 12 which contains a thermometer and flow meter. The isokinetic extraction of the sample will be set on the basis of the gas speed measurements carried out before the sampling.

After the sampling the adsorption device 1 is unscrewed from the probe 8 and gel box 10, and the thermoelement is replaced by a screw stopper. In order to process the sample, the adsorption device is attached to the extraction apparatus 11 as shown in FIG. 3. The probe 8 is rinsed inside with extraction agent, for example dichloromethane, and the rinse liquid is transferred to the extraction apparatus 11. Besides the rinse liquid, extraction agent in a suitable quantity is added in the extraction apparatus 11. The extraction agent is then heated so that it evaporates. At the top of the apparatus 11 a cooler has been placed where the evaporated extraction agent will condense and run down into the adsorption device. The sample in the adsorption device will then be extracted. The extraction apparatus 11 works on the soxhlet principle, that is, by means of several rinses with stripped solvent. When the processing procedure has been completed, the sample is collected in the flask at the bottom of the extraction apparatus 11 along with the extraction agent, and the adsorption device 1 contains regenerated adsorbents. One can thus use the adsorption device 1 for sampling again after drying without replacing the adsorbents. The sample collected can now be handled in accordance with conventional techniques, and analyses can be carried out quantitatively and qualitatively by means of known chromatography and mass spectrometry methods.

Tests

Several tests were conducted with the equipment as specified for the invention in an anode factory. For comparison purposes, the same tests were also done in accordance with the "Lurgi method" mentioned above.

Figure 4:
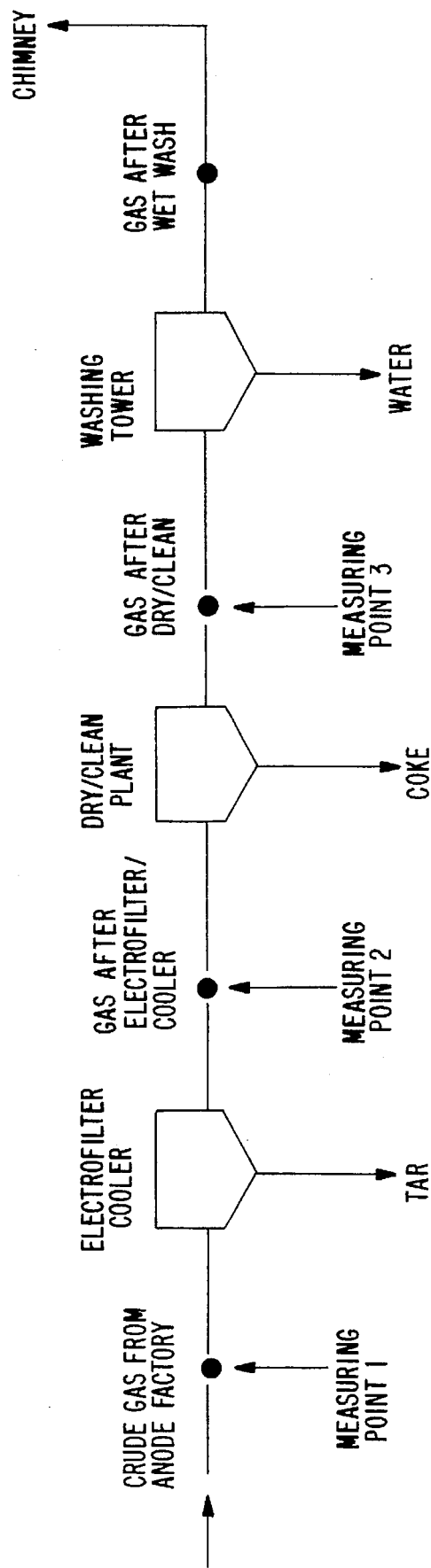
FIG. 4 is a flow diagram for a purification plant.

The tests were conducted in the exhaust gas from anode furnaces. The gas from these furnaces was cleaned by three different types of purification plant connected in series. FIG. 4 shows a flow diagram for the purification plants with the sampling/measurement points indicated.

Three parallel sets of samples were taken (I, II and III) with the new equipment at measuring points 1, 2 and 3 of FIG. 4 to determine the tar content and the content of PAH. Concurrently with two of these samplings, samples were taken in accordance with the "Lurgi method" to determine the content of tar at the measuring points 1 and 2, and once at the measuring points 2 and 3. The results are shown in Table 1.

Throughout the test, the adsorption device in the equipment according to the invention consisted of two middle pieces plus top and bottom, where the upper middle piece contained the main adsorbent, Tenax GC 60/80 mesh with glass wool, above and below, and the lower middle piece functioned as a control layer and was filled with silica gel.

TABLE 1

Determination of tar content (mg tar/Nm$^3$ dry gas) and PAH content (mg PAH/Nm$^3$ dry gas)

| Measuring point | Sample No. | I | II | III |
|---|---|---|---|---|
| 1 | New equipment, PAH | 120 | 174 | 224 |
|   | New equipment, tar (a) | 325 | 493 | 665 |
|   | New equipment, tar (b) | 317 | 427 | 562 |
|   | "Lurgi method" | 196 | 475 | — |
| 2 | New equipment, PAH | 52.3 | 59.3 | 83.4 |
|   | New equipment, tar (a) | 126 | 141 | 168 |
|   | New equipment, tar (b) | 60 | 126 | 63 |
|   | "Lurgi method" | 127 | 80 | 144 |
| 3 | New equipment, PAH | 35.5 | 44.2 | 63.1 |
|   | New equipment, tar (a) | 89 | 99 | 126 |
|   | New equipment, tar (b) | 60 | 44 | 91 |
|   | "Lurgi method" | — | — | 69 |

"New equipment, PAH" indicates the quantity of PAH determined by the equipment as specified for the present invention, with methylene chloride used as an extraction agent.
"New equipment, tar (a)" indicates that the tar content was determined with the equipment as specified for the present invention, with methylene chloride used as the extraction agent.
"New equipment, tar (b)" indicates that the tar content was determined with the equipment as specified for the present invention, with methylene chloride used as the extraction agent, and toluene added to the extraction solution for evaporation.
"Lurgi method" indicates that the tar content was determined by the Lurgi method, where the solvent used was toluene.

In addition to the PAH content determined with "New equipment, PAH" in Sample No. 2, gas chromatography analysis (GC) found respectively 9.5, 9.5 and 10.6 mg/NM$^3$ dry gas light organic components at the measuring points 1,2 and 3. Furthermore, another test revealed that all the PAH in the adsorption device has been captured by the main adsorbent, which shows that the adsorption agent provides adequate separation of PAH.

The ratio between the tar content and PAH content determined by "New equipment, tar (a)", where the tar content was determined by weighing the sample after the evaporation of methylene chloride, and where the PAH content was determined by GC analysis, was respectively 2.7–3.0, 2.0–2.4 and 2.0–2.5 at the measuring points 1, 2 and 3. It is reasonable to expect the ratio to be highest at Measuring Point 1, where the gas is unpurified, because a number of heavier particulate components cannot be analysed by the GC method.

When toluene is added to the extraction solution for evaporation ("New equipment, tar (b)"), the temperature at the end of the evaporation process is substantially higher than it is for the evaporation of the original extraction solution ("New equipment, tar (a)"). The reason for this is that the boiling point of methylene chloride is 40° C., while that of toluene is 110.6° C. The results with "New equipment, tar (b)" therefore exhibit a lower concentration than those with "New equipment, tar (a)" because the lighter PAH components have been expelled during the evaporation of the toluene. This is most clearly evident at the measuring points 2 and 3, where the heavier components have already been separated in the electrofilter. Here too the variations in the three samples are relatively large. This shows that the evaporation method with toluene leads both to greater systematic errors and random errors after the electrofilter, where the bulk of the particulate material has been removed.

The results using the "Lurgi method" also show relatively large variations at the same measuring points, and systematically lower values than when "New equipment, tar (a)" is used.

This test shows that when methylene chloride alone is used as a solvent, the tar components are measured very satisfactorily by the new sampling equipment.

We claim:

1. Sampling and extraction equipment, comprising:
   an adsorption device comprising a bottom piece, a top piece, at least one middle piece connected between said bottom piece and said top piece, and a solid adsorbent sandwich structure contained within said bottom piece, said top piece and said at least one middle piece, said adsorbent device further comprising an inlet and an outlet;
   a sampling arrangement comprising a temperature measurement device connectable with said adsorption device for measuring the temperature thereof, a sampling device connectable with said inlet of said adsorption device for providing a sample to said adsorption device and a humidity removal device connectable with said adsorption device for removing water from a sample; and
   an extraction device directly connectable with said inlet and said outlet of said adsorption device.

2. The equipment of claim 1, wherein said solid adsorbent sandwich structure comprises an adsorption agent filled in said at least one middle piece.

3. The equipment of claim 2, wherein said adsorption device further comprises separation elements separating said adsorption device into a plurality of layers, said separation elements having filtering material thereon.

4. The equipment of claim 3, wherein said separation elements each comprise netting or a grille.

5. The equipment of claim 2, wherein said bottom piece, said at least one middle piece and said top piece have sealing devices therebetween.

6. The equipment of claim 2, wherein said at least one middle piece comprises a plurality of middle pieces having a plurality of adsorption agents filled therein.

7. The equipment of claim 6, wherein each of said plurality of adsorption agents is identical.

8. The equipment of claim 6, wherein said plurality of adsorption agents are selected from the group consisting of aluminum oxide, silica gel and hydrophobic polymers.

9. The equipment of claim 2, wherein said adsorption agent is selected from the group consisting of aluminum oxide, silica gel and hydrophobic polymers.

10. The equipment of claim 1, wherein a heating element is connected to said adsorption device.

11. The equipment of claim 1, wherein said bottom piece, said at least one middle piece and said top piece are attached to one another by a clamping bolt arrangement.

12. The equipment of claim 1, wherein each of said bottom piece, said at least one middle piece and said top piece are cylindrical and connected by threads to each other.

13. The equipment of claim 1, wherein said bottom piece, said at least one middle piece and said top piece define a housing and comprise a material selected from the group consisting of metal, teflon, plastic and glass.

14. The equipment of claim 13, wherein said material is steel.

15. The equipment of claim 1, wherein said adsorption device has an aperture therein and said temperature measurement device of said sampling arrangement comprises a thermoelement insertable in said aperture.

16. The equipment of claim 1, wherein said sampling device of said sampling arrangement comprises a probe that is connectable with said inlet of said adsorption device and that is contactable with an object to be sampled.

17. The equipment of claim 1, wherein said humidity removal device of said sampling device comprises a pump connected to a gel box, said gel box being connectable with said outlet of said adsorption device.

18. The equipment of claim 17, wherein said pump is connected to a gas clock, said gas clock comprising a thermometer and a flow meter.

19. The equipment of claim 1, wherein said extraction device defines a means operating on the soxhlet principle for extracting a sample from said adsorption device.

20. The equipment of claim 1, and further comprising a microprocessor operating means for automatically operating said sampling arrangement together with said adsorption device.

21. The equipment of claim 1, and further comprising a closed container containing said adsorption device and said sampling arrangement therein.

22. Sampling equipment, comprising:
   an adsorption device comprising a bottom piece, a top piece, at least one middle piece connected between said bottom piece and said top piece, and a solid adsorbent sandwich structure contained within said bottom piece, said top piece and said at least one middle piece, said adsorbent device further comprising an inlet and an outlet; and
   a sampling arrangement comprising a temperature measurement device connectable with said adsorption device for measuring the temperature thereof, a sampling device connectable with said inlet of said adsorption device for providing a sample to said adsorption device and a humidity removal device connectable with said adsorption device for removing water from a sample.

23. The equipment of claim 22, wherein said sampling device of said sampling arrangement comprises a probe that is connectable with said inlet of said adsorption device and that is contactable with an object to be sampled.

24. The equipment of claim 22, wherein said humidity removal device of said sampling device comprises a pump connected to a gel box, said gel box being connectable with said outlet of said adsorption device.

25. The equipment of claim 24, wherein said pump is connected to a gas clock, said gas clock comprising a thermometer and a flow meter.

* * * * *